United States Patent [19]

Reuther et al.

[11] 4,447,448

[45] May 8, 1984

[54] WOOD PRESERVATIVE

[75] Inventors: Wolfgang Reuther, Heidelberg; Hans-Volker Borck, Baden-Baden, both of Fed. Rep. of Germany

[73] Assignee: BASF Aktiengesellschaft, Fed. Rep. of Germany

[21] Appl. No.: 449,317

[22] Filed: Dec. 13, 1982

[30] Foreign Application Priority Data

Dec. 29, 1981 [DE] Fed. Rep. of Germany ....... 3151806

[51] Int. Cl.$^3$ .................. A01N 43/08; A01N 33/02
[52] U.S. Cl. ................................ 424/285; 424/325
[58] Field of Search .............................. 424/285, 325

[56] References Cited

U.S. PATENT DOCUMENTS

3,993,772 11/1976 Pommer et al. ................ 424/285

OTHER PUBLICATIONS

Nachrichter aus Chemie, Technik and Lab. vol. 26, No. 3 (1968), pp. 117–118.

*Primary Examiner*—Jerome D. Goldberg
*Assistant Examiner*—John W. Rollins
*Attorney, Agent, or Firm*—Keil & Witherspoon

[57] ABSTRACT

A wood preservative comprises a mixture of
  A. N-cyclohexyl-N-methoxy-2,5-dimethyl-furan-3-carboxamide and
  B. tris-(N-cyclohexyl-diazeniumdixyo)-aluminum.

A process for treating wood with this mixture is also described.

2 Claims, No Drawings

WOOD PRESERVATIVE

The present invention relates to a wood preservative containing a mixture of active ingredients, and to a process for treating wood with this mixture.

The use of N-cyclohexyl-N-methoxy-2,5-dimethyl-furan-3-carboxamide for protecting wood against attack by wood-destroying fungi, such as *Coniophora cerebella, Poria monticola, Coriolus versicolor* and *Lenzites trabea*, is disclosed in U.S. Pat. No. 3,993,772. However, for effective protection, relatively high concentrations have to be used. Moreover, the stated compound is insufficiently effective against fungi which cause wood to discolor, such as *Pullularia pullulans* or *Sclerophoma pityophila*.

It has moreover been disclosed that tris-(N-cyclohexyl-diazeniumdioxy)-aluminum may be used to control wood-destructive fungi, such as *Coniophora cerebella, Merulius Lacrimans, Poria monticola, Lentinus Lepideus* and the like (Nachrichten aus Chemie Technik und Laboratorium, 26 (1968), No. 3, 117). However, this compound has the disadvantage of a serious weakness of effect on a very important wood-destroying fungus, *Coriolus versicolor*, so that very high concentrations have to be used for proper protection. In the case of tris-(N-cyclohexyl-diazeniumdioxy)-aluminum this is particularly undesirable and poses a major problem, since the compound is sparingly soluble in gasoline fractions and hence only solvent mixtures high in aromatics can be used to prepare a solution. Moreover, this low solubility often causes undesirable crystallization of the active ingredient on the surface of the wood. A further disadvantage, when using the alkyd resin-based paints and impregnants conventionally employed in wood preservation, is that the compound substantially delays the drying of the paint films, since the active ingredient is a very effective antioxidant (German Pat. No. 1,092,005).

We have found that a mixture of

A. N-cyclohexyl-N-methoxy-2,5-dimethyl-furan-3-carboxamide and

B. tris-(N-cyclohexyl-diazeniumdioxy)-aluminum exhibits a fungicidal activity greater than that of the individual ingredients, ie. a synergistic effect occurs. The ratio in which the active ingredients are mixed may vary within wide limits. For example, an excellent effect in controlling wood-destroying fungi is achieved with a weight ratio of A:B of from 1:3 to 3:1, especially 1:1.

The weight ratios of 1:3 and 3:1 were chosen because at these ratios there is marked synergism, whilst outside this range, for example at a ratio of 1:5 or 5:1, only a slight synergism, if any, is detectable. On the other hand, within the stated range, for example at a ratio of 1:2 or 2:1, a good synergistic effect, as with ratios of 1:3 and 3:1, is observed.

The novel mixtures of active ingredients may be used in formulations such as solutions, emulsions, pastes and oil dispersions. In general, the formulations contain from 0.1 to 90, preferably from 0.25 to 50, % by weight of the active ingredient mixture.

Depending on the type of wood and the intended use of the preserved wood, from 0.05 to 5, preferably from 0.1 to 2, kg of active ingredient mixture are applied per $m^3$ of wood. The upper limit is in general determined by economic considerations, and may in certain cases be even higher than stated above.

The active ingredient mixture is applied, for example in an oily or aqueous form, by brushing, spraying, atomizing or dipping. The amounts employed in these processes depend on the end use of the concentration of active ingredient but are in general from 75 to 350, preferably from 100 to 200, g of the active ingredient mixture per $m^2$ of wood surface. Primers and paints for wood may contain, for example, from 0.5 to 3.5% by weight of the mixture.

Particularly effective preservation of wood is achieved if the wood is impregnated with the mixture of active ingredients in an autoclave, kettle or chamber using special technical processes, for example the vacuum process, vacuum/pressure process or double vacuum process. To preserve wood-base material, the mixture of active ingredients can be added during manufacture of such materials, for example by being added as an emulsion, or undiluted, to the binder or adhesive, for instance in amounts of from 1.5 to 6% by weight, based on the adhesive.

To broaden the spectrum of action or to achieve special effects, other fungicides, insecticides and other active ingredients may be added to the mixture according to the invention. Particularly advantageous additional ingredients are the following compounds: trialkyl-tin compounds, methylene-bis-thiocyanate, 2-halobenzoic acid anilides, N,N-dimethyl-N'-phenyl-(N-fluoromethylthio)-sulfamide, N-phenyl-N,N'-dimethyl-N'-fluorodichloromethyl-thiosulfonyldiamide, methyl benzimidazole-2-carbamate, 2-thiocyanomethyl-thiobenzothiazole, copper naphthenate, 8-hydroxyquinoline or its solubilized copper salt, N-trichloromethylthio-tetrahydrophthalimide, N-trichloromethyl-thiophthalimide, N-(1,1,2,2-tetrachloroethylthio)-tetrahydrophthalimide, N,N-dimethyl-N'-p-tolyl-N'-dichlorofluoromethylthiosulfamide, 1-[2-(2,4-dichlorophenyl)-4-ethyl-1,3-dioxolan-2-yl-methyl]-1H-1,2,4-triazole and 1-[2-(2,4-dichlorophenyl)-4-propyl-1,3-dioxolan-2-yl-methyl]-1H-1,2,4-triazole and tetrachloroisophthalodinitrile.

EXAMPLE 1

Determination of the minimum inhibitory concentration in respect of wood-destroying fungi The method is used for determining the prophylactic action of wood preservatives in respect of wood-destroying fungi from the Basidiomycetes class.

Similar wood blocks (5×2.5×1.5 cm), which had been dried to constant weight at 103° C., were completely impregnated with graduated amounts of the candidate wood preservative, dried, washed in running water (so as to wash the mixture of active ingredients out of the wood) and exposed, in glass dishes, to attack by cultures of wood-destroying Basidiomycetes. Malt agar (containing 4% of malt extract) was used as the nutrient medium for the fungi. The active ingredients were dissolved or suspended in isopropanol. The destruction of the wood brought about by the fungal attack was assessed in terms of the weight loss of the samples of wood; a weight loss of 2% or more was assessed as destruction of the wood.

The results recorded are a lower concentration of active ingredient, just insufficient to prevent destruction of the wood, and an upper concentration of active ingredient, at which destruction of the wood is no longer detectable and accordingly complete preservation has been achieved. For assessing a wood preservative in practical usage, it is always the upper concentration (minimum inhibitory concentration MIC), after washing out, which is relevant.

Determination of the minimum inhibitory concentration in respect of wood-destroying fungi, after washing out (in kg of active ingredient per m³ of wood)

Active ingredient A = N-cyclohexyl-N-methoxy-2,5-dimethyl-furan-3-carboxamide

Active ingredient B = tris-(N-cyclohexyl-diazeniumdioxy)-aluminum

| Active ingredient | Coniophora puteana | Coriolus versicolor |
|---|---|---|
| A | 0.1–0.3 | 0.05–0.12 |
| B | 0.4–0.8 | about 7 |
| Active ingredient mixture A:B = 1:1 | 0.05–0.1 | 0.1–0.2 |

The result of the experiment shows that a 1:1 (by weight) mixture of active ingredients A and B has markedly greater activity than the individual active ingredients but in particular that the weakness of B as an agent for controlling *Coriolus versicolor* is overcome by admixture of A.

EXAMPLE 2

A = N-cyclohexyl-N-methoxy-2,5-dimethylfurancarboxamide

B = tris-(N-cyclohexyl-diazeniumdioxy)-aluminum

To demonstrate the synergistic action in the claimed range, the minimum inhibitory concentrations (MIC) of A and B were determined in agar nutrient media. The MIC's of A and B were compared with those of mixtures of A and B. The synergism was determined by the method described by Kull et al. (F. C. Kull, P. C. Eismann, H. D. Sylvestrowicz and R. J. Mayer, Applied Microbiol. 9 (1961), 538 et seq.).

In this method:

$$\frac{Q_A}{Q_a} + \frac{Q_B}{Q_b} = X$$

where
X = 1 means additivity
X > 1 means antagonism
X < 1 means synergism
$Q_a$ = MIC of substance A.
$Q_b$ = MIC of substance B.
$Q_A$ = Concentration of substance A in mixture A/B at which microbial growth is suppressed.
$Q_B$ = Concentration of substance B in mixture A/B at which microbial growth is suppressed.

The mixtures of active ingredient, dissolved in acetone, were added to a warm malt agar. The agar was poured into Petri dishes and, after solidification, was inoculated with a mycelium of *Coriolus versicolor* and kept under controlled climatic conditions (20° C., 90% atmospheric humidity).

TABLE

| | Test organism: Coriolus versicolor | | | | | |
|---|---|---|---|---|---|---|
| Weight ratio A/B | MIC ppm | $Q_a$ | $Q_A$ | $Q_b$ | $Q_B$ | X |
| 10/0 | 20 | 20 | 20 | 200 | 0 | |
| 3/1 | 20 | 20 | 15 | 200 | 5 | 0.77 |
| 1/1 | 20 | 20 | 10 | 200 | 10 | 0.55 |
| 1/3 | 50 | 20 | 12.5 | 200 | 37.5 | 0.81 |
| 0/10 | 200 | 20 | 0 | 200 | 200 | |

EXAMPLE 3

| Typical formulation | |
|---|---|
| N—Cyclohexyl-N—methoxy-2,5-dimethyl-furan-3-carboxamide | 1.0% by weight |
| Tris-(N—cylohexyl-diazeniumdioxy)-aluminum | 1.0% by weight |
| gamma-Hexachlorocyclohexane | 0.5% by weight |
| Dryer (metal salts of fatty acids) | 0.25% by weight |
| Alkyd resin (100% strength, ie. calculated without solvent) | 12% by weight |
| Aromatic and aliphatic hydrocarbons (boiling range 180–220° C.) | 85.25% by weight |
| | 100.00% by weight |

Correspondingly, oily wood preservatives were prepared with from 0.25 to 5% by weight of the active ingredient mixture A+B, the weight ratio A:B being varied within the limits stated earlier (from 3:1 to 1:3).

Corrosion inhibitors may also be added to the wood preservative.

To achieve color effects, finely divided inorganic or organic pigments, or oil-soluble dyes, can be incorporated into the preservatives. To prepare water-repellent impregnating paints, water-repellents such as metal stearates or waxes may be added to the wood preservatives.

We claim:
1. A composition for protecting wood against attack by wood-destroying fungi comprising a mixture of
   (A) N-cyclohexyl-N-methoxy-2,5-dimethyl-furan-3-carboxamide
and
   (B) tris-(N-cyclohexyl-diazeniumdioxy)-aluminum in a weight ratio of A to B of from about 1:3 to 3:1.
2. A method of protecting wood against attack by wood-destroying fungi comprising contacting the wood with a mixture of
   (A) N-cyclohexyl-N-methoxy-2,5-dimethyl-furan-3-carboxamide
and
   (B) tris-(N-cyclohexyl-diazeniumdioxy)-aluminum in a weight ratio of A to B of from about 1:3 to 3:1.

* * * * *

UNITED STATES PATENT AND TRADEMARK OFFICE
CERTIFICATE OF CORRECTION

PATENT NO. : 4,447,448
DATED : May 8, 1984
INVENTOR(S) : Wolfgang REUTHER et al.

It is certified that error appears in the above-identified patent and that said Letters Patent is hereby corrected as shown below:

IN THE ABSTRACT

Line 4, correct the spelling of "diazeniumdioxy".

Signed and Sealed this

Eighteenth Day of September 1984

[SEAL]

Attest:

GERALD J. MOSSINGHOFF

Attesting Officer

Commissioner of Patents and Trademarks